United States Patent
Spykerman et al.

(10) Patent No.: US 12,059,222 B2
(45) Date of Patent: Aug. 13, 2024

(54) ROBOTIC SURGICAL METHODS AND APPARATUSES

(71) Applicant: Sudhir Prem Srivastava, Haryana (IN)

(72) Inventors: Rachel R. Spykerman, Los Altos, CA (US); Michael G. Fourkas, Los Altos, CA (US); Daniel J. Solomon, Los Altos, CA (US); Jeffrey J. Barry, Los Altos, CA (US); Ruchi Dana, Los Altos, CA (US); Fred R. Seddiqui, Los Altos, CA (US)

(73) Assignee: Sudhir Prem Srivastava, Haryana (IN)

(*) Notice: Subject to any disclaimer, the term of this patent is extended or adjusted under 35 U.S.C. 154(b) by 273 days.

(21) Appl. No.: 17/671,398

(22) Filed: Feb. 14, 2022

(65) Prior Publication Data

US 2022/0160443 A1    May 26, 2022

Related U.S. Application Data

(63) Continuation of application No. PCT/US2020/046077, filed on Aug. 13, 2020.

(Continued)

(51) Int. Cl.
| | |
|---|---|
| *A61B 34/30* | (2016.01) |
| *B25J 9/16* | (2006.01) |
| *G06N 3/045* | (2023.01) |
| *G06T 7/00* | (2017.01) |
| *G06T 7/50* | (2017.01) |
| *G06T 7/70* | (2017.01) |

(52) U.S. Cl.
CPC ............. *A61B 34/30* (2016.02); *B25J 9/1697* (2013.01); *G06N 3/045* (2023.01); *G06T 7/0012* (2013.01); *G06T 7/50* (2017.01); *G06T 7/70* (2017.01)

(58) Field of Classification Search
CPC .. A61B 34/30; G06T 7/50; G06T 7/70; G06T 7/0012; G06N 3/045; B25J 9/1697
See application file for complete search history.

(56) References Cited

U.S. PATENT DOCUMENTS

| | | | |
|---|---|---|---|
| 9,792,531 B2 * | 10/2017 | Georgescu | G06F 18/24 |
| 11,393,114 B1 * | 7/2022 | Ebrahimi Afrouzi | |
| | | | G01C 21/3848 |

(Continued)

FOREIGN PATENT DOCUMENTS

| | | |
|---|---|---|
| WO | WO2019021058 A2 | 1/2019 |
| WO | WO2019071189 A2 | 11/2019 |

OTHER PUBLICATIONS

Nilwong et al., "Deep Learning-Based Landmark Detection for Mobile Robot Outdoor Localization", MDPI, Machines, Accepted: Apr. 16, 2019; Published: Apr. 18, 2019, 14 pages. https://doi.org/10.3390/machines7020025.

*Primary Examiner* — Jaime Figueroa
*Assistant Examiner* — Mohamad O El Sayah
(74) *Attorney, Agent, or Firm* — SZDC Law PC

(57) ABSTRACT

Robotic surgical methods and apparatuses, including systems, for determining positioning information using a combination of AI landmark-identification and visual imaging. Also described herein are methods and apparatuses for determining how to train the AI. Also described herein are end effector devices that may be used with any of the robotic surgical methods and apparatuses. Also described herein designs and techniques incorporating AR into robotic surgical procedures.

20 Claims, 10 Drawing Sheets

Related U.S. Application Data

(60) Provisional application No. 62/886,302, filed on Aug. 13, 2019.

(56) References Cited

U.S. PATENT DOCUMENTS

| | | | |
|---|---|---|---|
| 2017/0239007 A1 | 8/2017 | Crawford et al. | |
| 2018/0075602 A1* | 3/2018 | Shen | G06T 7/62 |
| 2018/0125584 A1 | 5/2018 | Lang | |
| 2018/0253837 A1* | 9/2018 | Ghesu | G06T 7/0012 |
| 2018/0296281 A1* | 10/2018 | Yeung | A61B 34/32 |
| 2019/0043003 A1 | 2/2019 | Fisher et al. | |
| 2019/0046276 A1 | 2/2019 | Inglese et al. | |
| 2019/0289282 A1* | 9/2019 | Briggs | H04N 13/239 |
| 2020/0342600 A1* | 10/2020 | Sjöstrand | A61B 6/032 |
| 2020/0387706 A1* | 12/2020 | Zur | G06T 7/0012 |
| 2021/0267440 A1* | 9/2021 | Lin | A61B 34/35 |
| 2021/0290317 A1* | 9/2021 | Sen | A61B 34/70 |

* cited by examiner

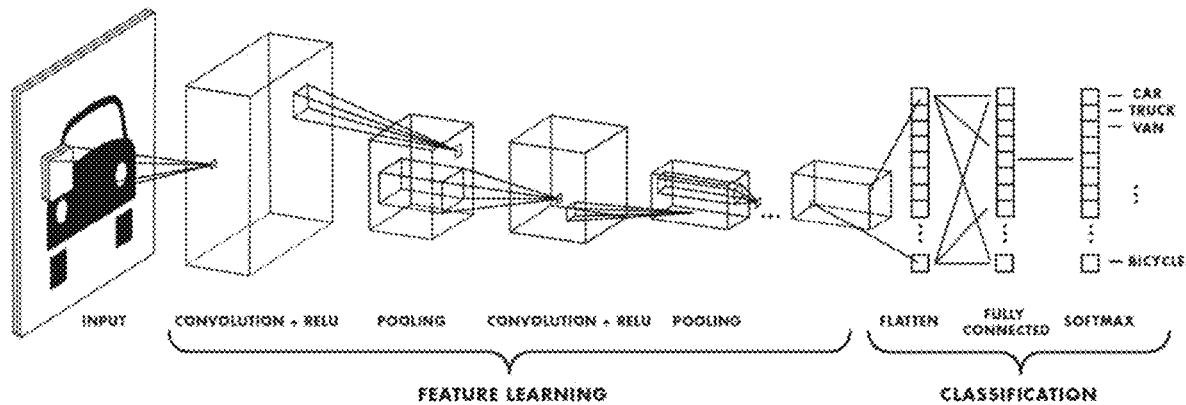
FIG. 5
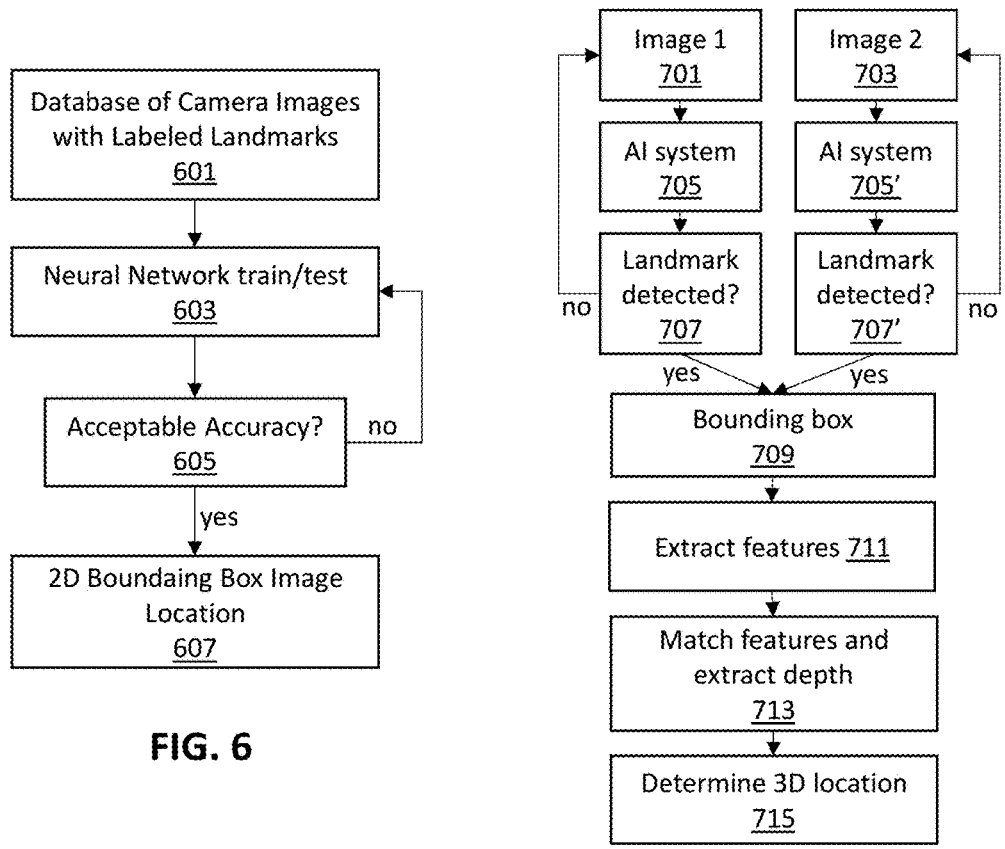
FIG. 6
FIG. 7

ROBOTIC SURGICAL METHODS AND APPARATUSES

CROSS REFERENCE TO RELATED APPLICATIONS

This application is a Continuation of and claims priority to PCT/US2020/046077 filed 13 Aug. 2020 which in turn claims priority from U.S. Provisional 62/886,302 filed 13 Aug. 2019, the entirety of which are both hereby incorporated by reference

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein relate generally to tools and system for facilitating orthopedic procedures.

BACKGROUND

Robotic devices may be useful to assist in the performance of surgical procedures. A robotic device typically includes a moveable arm that comprises one or more linkages. The arm has a free distal end that can be placed and moved with a very high degree of accuracy. A surgical instrument designed to be applied to the surgical site is typically attached to the free end of the arm. The practitioner is able to precisely position the arm so as to precisely position the surgical instrument at the site on the patient at which the instrument is to perform a medical or surgical procedure. One advantage of using a robotic system to hold the instrument is that the system arm, unlike the arms and hands of a surgeon, are not subjected to muscle strain or neurological actions like twitching. Thus, in comparison to hand-held instruments, a medical robotic system may hold an instrument steady, or move the instrument along a defined path with a higher degree of accuracy.

Some robotic surgical systems are designed to be used with surgical navigation systems. A surgical navigation system is a system that is able to generate data that provides a relatively precise indication of the surgical instrument relative to the location of the patient against which the instrument is applied. When a surgical robotic system is provided with the data indicating the position of the instrument relative to the patient, the robotic system may be able to automatically position the instrument to ensure that it is applied to the tissue of the patient against which the instrument is supposed to be applied. Even when the patient position is changed during the surgery, the surgical robotic system may reposition itself relative to the patient's surgical site with the help of this surgical navigation system. This substantially eliminates the likelihood that the instrument will be applied to tissue against which the instrument should not be applied. Very often, during the surgery, when the patient's body is moved, the robotic surgical system can reposition itself to point towards the surgical site by detecting the bony landmarks, this assists the surgeons to operate freely at the correct angle and avoid confusion due to change in patient surgical site.

Some medical robotic systems are designed to work in what is referred to as a "semi-autonomous" mode. In this mode of operation, the robotic system actuates the arm so as to cause the instrument to move against the patient's tissue in a preprogrammed path. This is useful if, for example, the instrument is a cutting device and the goal of the particular procedure is to remove a pre-defined section of the patient's tissue. By way of reference, if a robotic system operates in an "autonomous" mode of operation, the robot, once actuated, performs the procedure with essentially no input from the surgeon. In a "semi-autonomous" mode of operation, the practitioner may assert commands to control the operation of the robot. For example, some semi-autonomous robots are constructed so that, in order for the robot to displace the instrument, the practitioner must actuate a command by continually depressing a control button or switch associated with the robot. Upon the negation of the actuate command by the practitioner, the advancement of the instrument by the robot temporarily stops.

Some robotic systems are not traditional robots, in that once activated, they do not automatically move the attached instrument along a pre-programmed path of travel. These systems include control systems through which the practitioner enters commands indicating where the attached instrument is to be positioned, or the practitioner physically moves the arm while the arm retains positional referencing. This type of system actuates the system's arm/arms to cause the essentially simultaneous, real time, movement of the instrument. These robotics systems are considered to operate in a manual mode.

The system could also utilize multiple arms, some of which are automated or semi-automated, and some of which are manually operated. Or, one or more of the arms may switch functions between an automated, semi-automated or manual mode. For example, in an orthopedic joint replacement procedure, the practitioner may want the instrument, a cutting tool, to move in a programmed path in order to precisely shape the bone to which the instrument is applied. This precise bone shaping facilitates the precise fitting of the implant to the face of the bone exposed by the cutting tool, while minimizing healthy bone loss. However, there may be a situation in which, after the procedure begins, it becomes apparent that the instrument may collide with an object at the surgical site against which such contact is undesirable. This object may be tissue that has moved into the surgical site or a second instrument positioned at the site. In this situation, it is desirable for the practitioner to momentarily interrupt the programmed movement of the tool, manually control the tool to reposition the instrument, and then return the tool to the programmed movement.

Moreover, it is desirable that the relationship between the arms, instruments and the physiologic target are precisely known and controlled. In previous embodiments, pins and indexing arrays are attached to remote portions of healthy tissue in order to identify location. It is advantageous to use attachments only to tissue that is intended to be removed, or ideally not introduce any attachments but rather provide precise indexing with touch contact or vision systems. Further it is also desirable that the system support consists not just of robotic arms, but that the context of the procedure is available to the practitioner such that there are pre-procedure planning tools, executional tools and feedback tools to facilitate the procedure.

Described herein are system (apparatuses and devices) and methods that may address or ameliorate one or more disadvantages or limitations associated with the prior art, or to at least provide a useful alternative.

SUMMARY OF THE DISCLOSURE

The present invention relates to surgical methods and apparatuses that may include robotic, and in particular, artificial-intelligence (AI) assisted robotic apparatuses and methods. These apparatuses may be table-mounted (e.g., configured to mount a robotic member, such as a robotic arm, on a bed or surgical table). These apparatuses may provide navigation and/or treatment planning using an AI agent to identify landmarks, in particular, anatomical landmarks, to navigate the robotic device or to assist in navigation with the robotic device.

Also described herein are surgical apparatuses including end effectors for robotic surgical apparatuses that may be used with any of the robotic surgical systems and methods described herein. For example, an end effector for a robotic surgical system may include a drill or burr. The drill or burr may include one or more sensors to detect force (pressure, etc.), temperature (e.g., heat, etc.) or the like.

Also described herein are methods of operating robotic surgical devices. For example, described herein are method of operating a robotic surgical device, the method comprising: detecting one or more landmarks within an image of a first field of view of a camera associated with the robotic surgical device and within an image of a second field of view that overlaps with the first field of view using an artificial intelligence (AI); and determining the position of a robotic arm or a device held in the robotic arm by triangulating between the image of the first field of view and the image of the second field of view.

Any of these methods may include detecting pathological tissues from the first field of view and displaying an image of the image of the first field of view in which the pathological tissues are marked. Detecting pathological tissues may include determining from a pre-scan of the patient (e.g., from a plurality of CT and Mill scans) a classification and location of pathological tissues on a 3D model. In some variations, detecting one or more landmarks may include receiving CT and Mill scans to create a patient specific 3D model of a joint.

Any of these methods may include creating two separate neural networks to identify the one or more landmarks within the images of the first and second fields of view. For example, a first neural network may be trained from an input dataset comprising a pre-procedure CT scan and/or Mill data. The CT scan and/or Mill data may be from a plurality of different subjects. In some variations the second neural network may be trained from an input dataset of arthroscopic camera images from a plurality of different surgeries.

Any of these methods may include producing a bounding box around a pixel location of the one or more landmarks in each of the in the images of the first and second fields of view. As used herein a bounding box may be any shape (not limited to rectangular), and any appropriate size.

Any of these methods may include determining the position of the robotic arm or the device held in the robotic arm by triangulating between the image of the first field of view and the image of the second field of view comprises reconstructing a depth of the landmark relative to the robotic arm or the device held in the robotic arm.

Any of the methods described herein may also include continuously refining the AI to recognize the landmark.

In some variations, the method (or an apparatus configured to perform the method) may include selecting two or more landmarks to train the AI on, wherein at least one of the landmarks is selected to for having a feature with high variance and a second landmark is selected for having a feature with a low variance.

The machine learning (e.g., AI) agent may be periodically or continuously updated. For example, a method or apparatus as described herein may include continuously updating a database of optical images, MRI scans and CT scans used to train the AI.

As mentioned, because of the more accurate and adaptable AI-assisted guidance (e.g., by recognizing anatomical landmarks), any of these methods may be used with a table or bed mounted robotic arm. For example, any of these methods may include coupling the robotic surgical device to a table on which a patient is positioned.

For example, a method of operating a robotic surgical device may include: detecting one or more landmarks within an image of a first field of view of a camera associated with the robotic surgical device and within an image of a second field of view that overlaps with the first field of view using an artificial intelligence (AI); producing a bounding box around a pixel location of the one or more landmarks in each of the in the images of the first and second fields of view; and determining the position of a robotic arm or a device held in the robotic arm by triangulating between the pixel location in each of the images of the first and second fields of view.

Also described herein are systems that may perform any of the methods described herein. For example, a system may include: one or more processors; and a memory coupled to the one or more processors, the memory configured to store computer-program instructions, that, when executed by the one or more processors, perform a computer-implemented method comprising: detecting one or more landmarks within an image of a first field of view of a camera associated with the robotic surgical device and within an image of a second field of view that overlaps with the first field of view using an artificial intelligence (AI); and determining the position of a robotic arm or a device held in the robotic arm by triangulating between the image of the first field of view and the image of the second field of view.

For example, described herein are methods of operating a robotic surgical device and systems including non-transitory computer-executable instructions for performing these methods. For example, a method of operating (e.g., steering, guiding, etc.) a robotic surgical device may include: determining a position of one or more landmarks from an image of a first field of view of a camera associated with the robotic surgical device using a first neural network, further wherein the first neural network determines the depth of the one or more landmarks using an image of a second field of view that overlaps with the first field of view; and determining a surface normal for the one or more landmarks using a second neural network; and steering the robotic surgical device using the position and surface normal for the one or more landmarks. Any of these methods may include determining the position of a robotic arm of the robotic surgical device or of a device held in the robotic arm by triangulating between the image of the first field of view and the image of the second field of view.

All of the neural networks may operate in parallel, e.g., the first and second neural networks may operate in parallel.

Any of these methods may include determining the orientation of the one or more landmarks relative to the robotic arm using the surface normal and a camera angle of the camera. For example, the second neural network may be configured to determine the orientation of the one or more landmarks.

The image of the first field of view and the image of the second field of view may be arthroscopic images taken during the procedure. Determining the position of the one or more landmarks may include using a third neural network operating on one or more external scan images to detect a pre-planning position of the one or more landmarks and wherein the position of one or more landmarks comprises a combination of a position information from the first neural network and the pre-planning position from the third neural network.

Any of these methods may include detecting the one or more landmarks from the image of the first field of view of the camera using the first neural network. Any of these methods may include detecting the one or more landmarks from the image of the first field of view of the camera using a combination of the putative landmark detection from the first neural network and landmark detecting from the third neural network.

Determining the surface normal for the one or more landmarks using the second neural network may comprise using the image of the first field of view, the second field of view or both the first and second field of view. Determining the surface normal for the one or more landmarks using the second neural network may include combining surface normal information from the second neural network with surface normal information from a fourth neural network.

Any of these methods may include detecting pathological tissues from the first field of view and displaying an image of the image of the first field of view in which the pathological tissues are marked.

Detecting pathological tissues may comprise determining from a plurality of CT and MRI scans a classification and location of pathological tissues on a 3D model. For example, detecting one or more landmarks may comprise receiving CT and MRI scans to create a patient specific 3D model of a joint. A first neural network may be trained from an input dataset comprising a pre-procedure CT scan and/or Mill data. The CT scan and/or Mill data may be from a plurality of different subjects. The second neural network may be trained from an input dataset of arthroscopic camera images from a plurality of different surgeries.

As mentioned, any of these methods may include producing a bounding box around a pixel location of the one or more landmarks in each of the in the images of the first and second fields of view.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 5 shows the architecture of a system and method using AI to determine 3D position based on a set of images.

FIG. 6 schematically illustrates a method of training a system to identify landmarks in 2D images.

FIG. 7 schematically illustrates a method of determining the depth of a tool (e.g., the robotic arm, an end-effector device, etc.) using multiple images to triangulate to an identified (e.g., an AI-identified) target point.

DETAILED DESCRIPTION

The apparatuses and methods described herein include robotic systems and methods of operating them. In particular, described herein are robotic surgical methods and apparatuses, including systems, for determining positioning information using a combination of AI landmark-identification and visual imaging. Also described herein are methods and apparatuses for determining how to train the AI. Also described herein are end effector devices that may be used with any of the robotic surgical methods and apparatuses. These apparatuses (e.g., systems and devices) may include table-mounted robotic surgical systems that are configured to visually assist surgeons operating on patients, and may include one or more intelligent (e.g., artificial intelligence, or IA) agents that are configured to analyze per-scans and scans of the surgical region.

An apparatus (e.g., a system) may include single or multiple automated, semi-automated, and or manually controlled arm(s). An apparatus may include one or more components, features or sub-systems that may assist in controlling the arms, including indicating/controlling the positioning of the arms in 3D space. The system may include one or more location sensing features that identify the location of the arm(s) relative to a physiologic feature(s). In addition, the system may include one or more controllers (e.g., control modules) and planners (e.g., planning modules) that coordinate movement of the arms(s) and/or components held within the arms, such as end effectors or devices including one or more end effectors.

In some configurations the apparatus may include one or more arms that can automatically or semi-automatically position itself. In other instance that apparatus may have one or more arms that are manual positioned. In any of these configurations, the apparatus may know the position of one or more of the arms relative to the physiologic target.

Figure 1:
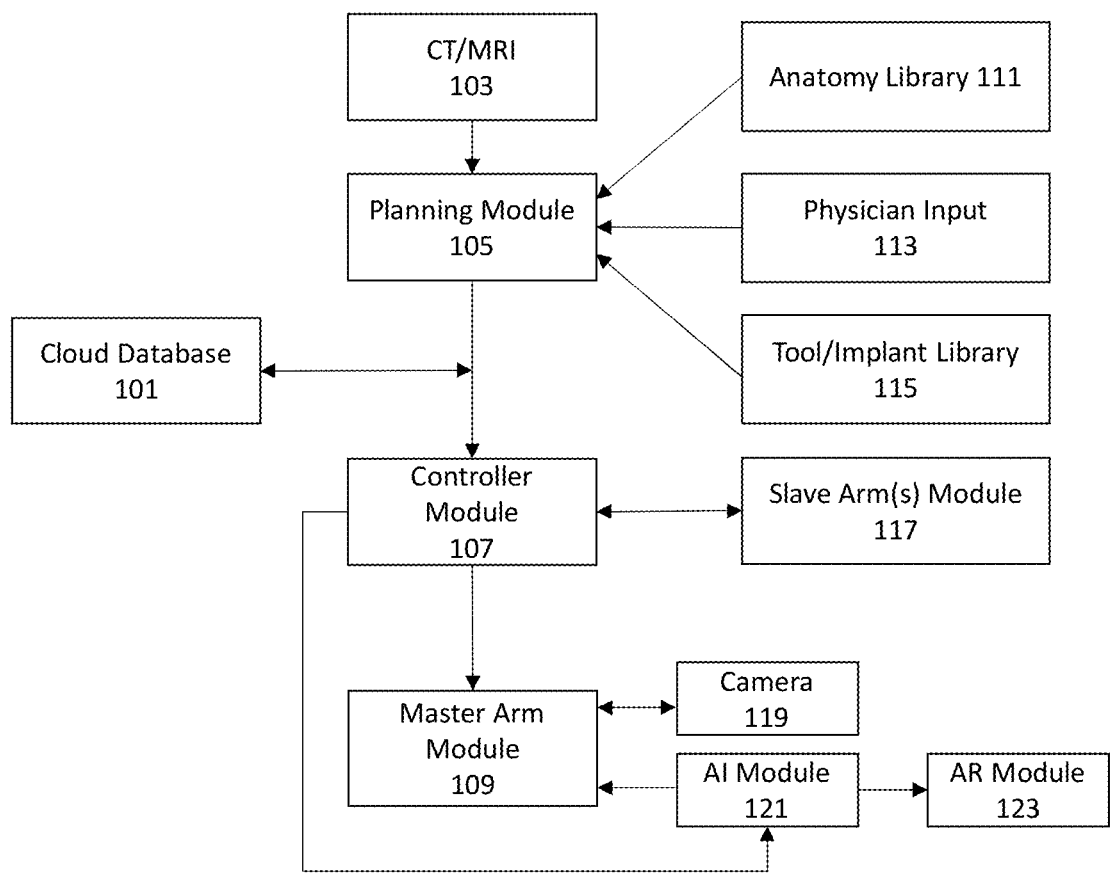
FIG. 1 is a schematic diagram showing an overview of one example of a system as described herein.

For example, FIG. 1 schematically illustrates one example of an apparatus. In this example, the apparatus includes a planning module 105 and a controller module 107. The planning module may receive input from a variety of different inputs, including patient-specific information from one or more sources of patient imaging and anatomy (e.g., a CT/MRI input 103). The planning module may receive input from an anatomy library that include one or more (or a searchable/referenced description of a plurality of different) anatomical examples of the body regions to be operated on by the apparatus, such as a body joint (knee, shoulder, hip, elbow, wrist), body lumen (bowel, large intestine, small intestine, stomach, esophagus, lung, mouth, etc.), vasculature, etc. The planning module may be configured to receive input from a physician, e.g., through one or more physician inputs 113, such as a keyboard, touchscreen, mouse, gesture input, etc. In some variations, the planning module may include one or more inputs from a tool/implant library 115. A tool/implant library may include functional and/or structural descriptions of the one or more tools that may be operated by the apparatus, including tools having end effectors for operating on tissue. The tools/implants may include cutting/ablating tools, cannula, catheters, imaging devices, etc. The tool/implant library may include a memory or other storage media storing the information on the tool/implant (for the tool/implant library) or the anatomy (for the anatomy library).

The planning module is described in greater detail below, but may provide instructions and/or command information to the controller to control or partially control the robotic arm(s) and/or devices/tools (including end effectors) held or manipulated by the robotic arm(s). For example, a planning module may pre-plan one or a series of movements controlling the operation of a robotic arm(s) and/or a device/tool/implant held in the robotic arm(s). In some variations the planning module may adjust the plan on the fly (e.g., in real or semi-real time), including based on the inputs, including but not limited to the physician input. In some variations the planning module may receive information from the camera 119 or other sensors on the robotic arm(s) and/or tool(s) held by the robotic arms (not shown).

A remote database (e.g., cloud database 101) may be in communication with the planning module and/or the controller module. The remote database may store and/or review/audit information to/from the planning module and/or the controller module. The remote database may provide remote viewing and/or archiving of operational parameters, including control instructions, planning instructions, inputs (anatomy inputs, physician inputs, tool/implant library inputs, etc.).

The controller module may control (and provide output) to the one or more arms, including one or more slave arm(s) via a slave arm(s) module 117. The controller module may also control the primary or principle robotic arm ('master' arm) via a master arm module 109. The master arm and/or one or more of the slave arm(s) may include a camera 119. The controller module may also communicate with an AI Module 121 that may receive input from the controller module and/or the planning module (not shown). The AI Module may communicate with an AR module (augmented reality module) 123, as shown.

The one or more arm(s) may be positioned so as not to interfere with the patient, physician, or other equipment. The apparatus may also be configured to easily store away equipment (e.g., components, sub-systems, etc.) that is/are not in use. In general, the equipment may have sufficient mechanical properties so that it can precisely access the surgical site without mechanical motion (e.g., deflection, vibration, etc.). For these reasons, the apparatus may have arms that can be mounted directly to table, yet be light enough that they can be removed and installed when needed. The arm may be suitable for mounting on any (or all) types of operating theater (OT) tables and multiple arms can be mounted to the table as per requirement on same or either side of the OT table to balance the weights of these arms with respect to the patient weight and other arm weights.

Figure 2:
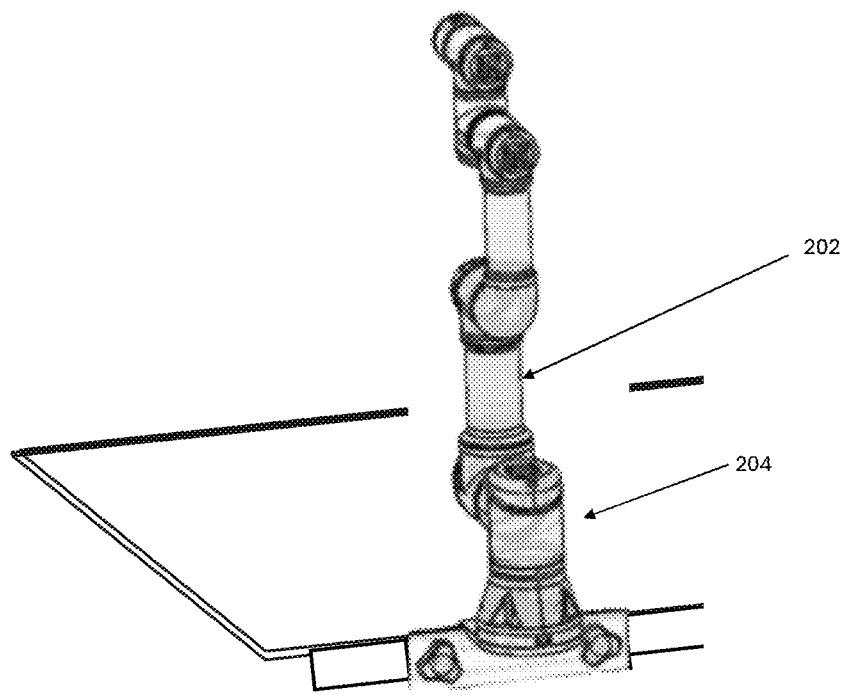
FIG. 2 is an example of a robotic arm mounted on a table.

For example, FIG. 2 illustrates one example of a robotic arm 202 (in this case, the master arm) mounted to a surgical table 204. As mentioned, any appropriate robotic arm may be used or adapted for use as described herein. The robotic arm may be mounted via a fixed connection (bolt, screw, strap, clamp, etc.). See, e.g., FIG. 12. In some variations, the robotic arm may be stabilized by a frame or frame portion that extend under the table, bed, etc. Additional robotic arm(s) may be affixed to the table or to a separate table or cart. Any of these apparatuses may identify the location of the arm(s) relative to the master arm.

For example, one or multiple robotic arms may be used in a procedure. In one modality a single (master) arm that has a precisely determined location relative to the physiologic target. The other robotic arms would then receive positional location from the master arm to know/position it relative to the master arm. In other configurations, there could be a primary arm for locating the system relative to the physiologic target, then some or all of the other arms could be used to provide supplemental information. Multiple arms could also be complementary in each providing locational information that compiled together gives precise information of all the elements of the system. In some modalities, location sensing elements are not attached to a robotic arm but are precisely placed relative to the physiologic feature.

For precision, the apparatuses described herein may advantageously physically touch the anatomic target as part of the guidance/control. Physical touch may exactly index the physiologic site in 3D space. This could be accomplished by having an end effector on a robotic arm (or held by the robotic arm) that is positioned against a physiologic landmark. The end effector may also be used to touch additional locations in order to provide additional information on the location and dimensions of the physiologic feature. Further, a tactile marker, such as a screw or other feature (or multiple screws and features), may be attached to the physiologic landmark so that the robotic arm could use the screw for precise positional location. The tactile marker (e.g., screw) could be on a portion of the bone that will be removed procedurally. In that way there would be no impact to healthy tissue by the attachment. One or more of the robotic arms could be physically attached to the screw(s) so that the absolute position is maintained regardless of repositioning of the joint. Thus, when during the surgery, if the patient's joint is moved, the robotic surgical system can reposition itself to point towards the surgical site. Sensing elements could also be incorporated. For instance, imaging could be used to detect the location of the patient, surgical team and other equipment which may be used to prevent the robotic arm from contacting them during motion. Other safety mechanisms that could be included instead of, or in addition to optical sensing could be force sensors that stop upon contact: and position, velocity, and acceleration limits.

Figure 3A:
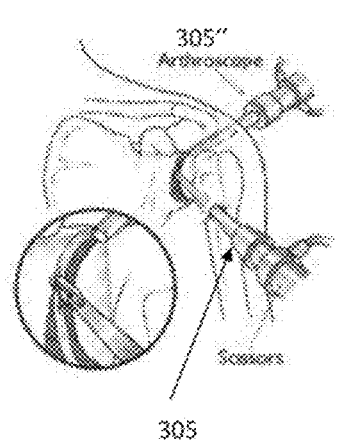
FIGS. 3A-3B illustrate the use of instruments by a robotic arm for placement into the tissue in exemplary procedures that may be performed on a patient.
Figure 3B:
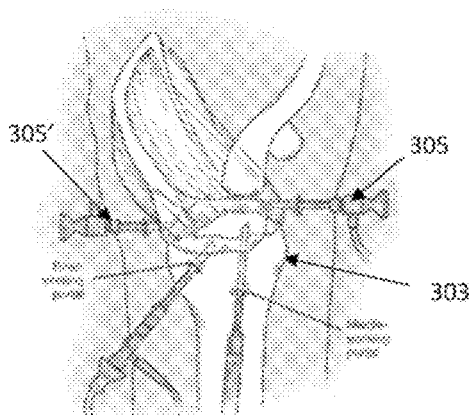

For example, FIGS. 3A-3B illustrate use of instruments (which may be held/driven by a robotic arm) 305, 305', 305" for placement into the tissue, including the use of touch for arm (e.g., master arm) location and/or surgical navigation. The instruments and/or robotic arms may be indexed to each other and/or to one or more anatomic or introduced (e.g., screw, etc.) landmark features 305.

Figure 3C:
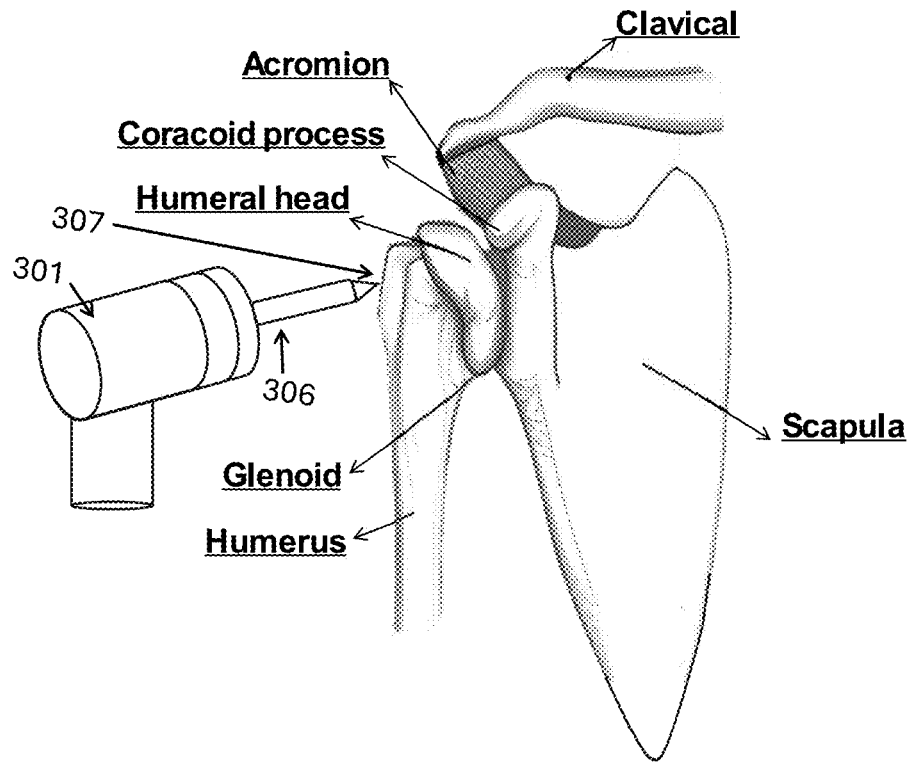
FIG. 3C is an example of using visual imaging for master arm location.

Alternatively and/or additionally, visual imaging may be used for determining positioning of the arm(s) (e.g., master robotic arm, etc.). For example, FIG. 3C shows an example of using visual imaging for master arm location. In FIG. 3C, a robotic arm 301 holds a device including a touch end effector 306 that contacts a bony landmark for the patient's arm 307. In general, the apparatuses and methods described herein may be configured to perform orthopedic procedures arthroscopically (through cannulation) and/or can be performed through open surgical procedures. In either case the procedure may be visualized by the physician. Visualization may be used in coordination with the localization of a robotic arm. As mentioned, in addition or alternatively to using touch for positioning, a visualization system (subsystem) may be used for position detection. The 2D image obtained from the arthroscopic camera can be used to identify physiologic landmarks. Various classical vision techniques can be used to identify particular landmarks by detecting 2D feature points (e.g., based on color, shape, orientation) unique to that landmark. Example feature extraction algorithms include SIFT (Scale-Invariant Feature Transform), ORB (Oriented FAST and Rotated BRIEF), and SURF (Speeded Up Robust Features).

Once the 2D feature points are detected for a landmark, a 3D position can be extracted by using a stereo camera projection algorithm. The 2D feature point may provide x and y locations in space, and z distance of the 3D position may be determined. Rather than analyzing only one image view of the detected landmark, a depth estimation can be determined by analyzing two views of the same landmark and tracking the displacement of detected features across these two images. The robotic arm may obtain the first image view of the landmark, 2D features of the landmark may then be extracted, and then the robotic arm may shift the arthroscopic camera horizontally by a small fixed distance to obtain the second view of the landmark (e.g., as part of a triangulation procedure). The 2D features of the landmark may then be extracted. Matching feature points across the two images may then be found, and the displacement between these points may be determined. A relationship of depth=1/displacement may allow the determination of the z distance of the 3D position. This is illustrated, for example, in FIG. 4.

Figure 4:
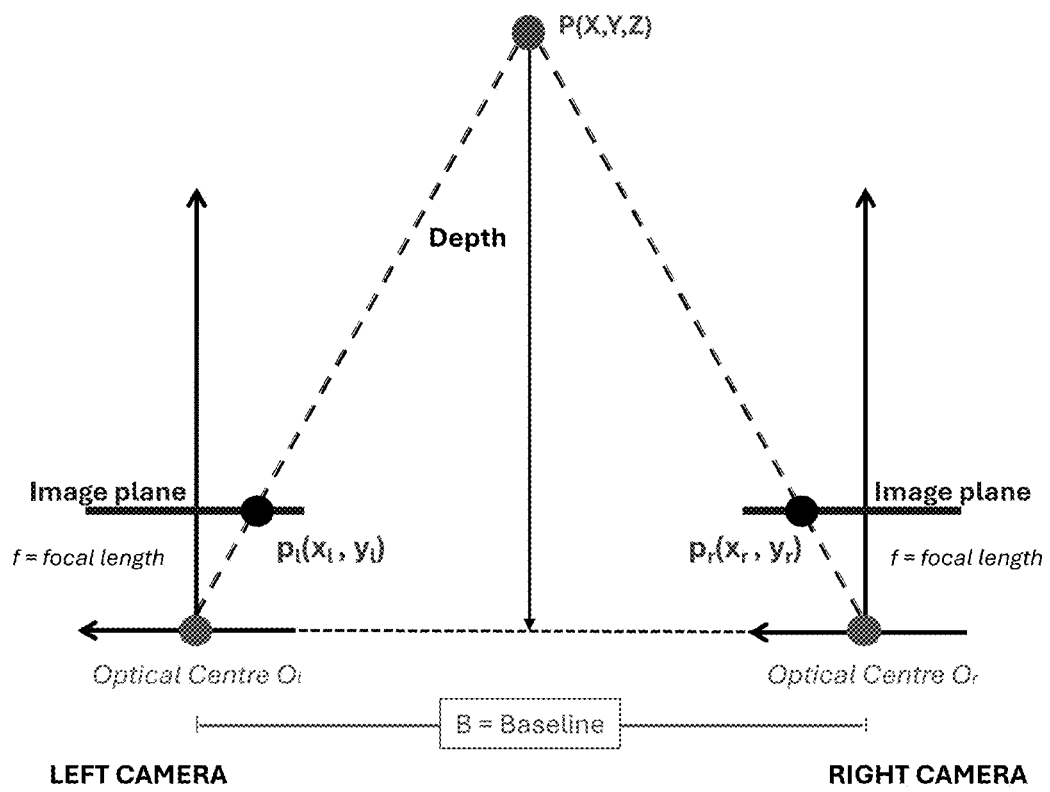
FIG. 4 illustrates one example of a method of determining depth of a target point using a visual imaging technique as described herein.

In this example, the visual imaging could also be coupled with one or more "touch" techniques as described above. A tool could touch the target tissue, and could, for example, have calibrated bands or have known physical dimensions. These could then be correlated to the pixels in the image and therefore provide calibrated indexing to the rest of the visible field. In FIG. 4, either the same camera may be used and moved between the right and left positions, or a separate left and right camera may be used, and may take images of a target positon (point P(x,y,z)) in space. As mentioned above, the x and y positions may be determined from the 2D image, and the changes based on a known separation between two or more images (e.g., left camera, right camera) may be used to determine the depth and therefore the z distance.

Using AI for Identifying Location

Artificial Intelligence (AI) based algorithms can be used in place of, or in conjunction with, classical vision techniques to further improve efficiency and accuracy of the robotic arm positioning in any of the apparatuses and methods described herein. In classical vision techniques, it may be difficult to generalize 2D features of a landmark across various patients, causing inaccuracies when determining the precise location of a landmark. AI can be employed by training a system across a large dataset of images where a ground truth is provided dictating the correct position of a particular landmark for every image. The ground truth is a bounding box drawn around the desired landmark in the training images that is to be detected. The trained system may then be tested on a separate database of new images, and the detections produced by the system are compared against the ground truth to determine the accuracy of that detection. The train and test steps are repeated until an acceptable accuracy is achieved.

For training an AI system using images, a deep neural network such as a Convolutional Neural Network (CNN) may be used to learn the key features of a landmark across the database of images. FIG. 5 illustrates the architecture of one example of a CNN. It takes as an input an image, and then assigns importance to key aspects in the image by creating weights and biases. The image is passed through several layers to extract different features, thereby creating various weights and biases. These weights and biases may be used to determine how well the network is trained by adjusting these values over many rounds of training and testing until an acceptable accuracy is achieved. Once a landmark has been correctly classified in an image, a bounding box may be produced as an output which provides an accurate pixel location of the landmark in the 2D image. From here, a vision camera projection algorithm such as the one described above, may be used to determine the depth portion of the 3D position.

By using AI to determine a 3D position of the robotic arm, calibration activities may not be required. Each procedure could also be used to further build the image database and improve the accuracy of the neural network. The trained neural network detects a region (landmark) within the current image (following a similar architectural flow depicted in FIG. 5) which is then used to determine a 3D position in space; this information may be used to determine relative position of the arm(s) to the body and/or each other. The example shown in FIG. 5 is a generic overview of a convolutional neural network; other ways of determining a bounding box may be used. An apparatus or method as described herein may include recording from real or simulated procedures. For example, a system may then be trained so that in procedures it recognizes location without calibration activities. Each procedure could be used to further build and refine the capability of the apparatus (e.g., the AI algorithm). Alternatively, or in conjunction, training could be performed using existing databases of physiologic information such as pre-procedure MRIs or CT scans.

Using AI in Pre-Procedure to Identify Pathological Tissues

In addition to using AI on the arthroscopic images obtained during the surgery, a CNN can be trained on CT scans and MRI images to aid in the pre-surgery analysis. The AI can be used in pre-procedure planning to visualize pathological tissues in a 3D model and then help the surgeon locate them during the surgery and further help remove these tissues during the procedure. In the case of Joint Replacement Surgeries, with the help of real or simulated procedures and further pre-procedure MRIs and CT Scans, the system could be trained to identify pathological tissues like osteophytes, calcific tendinitis, pannus formations and also check for synovitis, osteitis and bone erosions. Further, during surgical procedures, the AI system algorithm may be trained to recognize these pathological tissues and study their removal with safe margins from healthy tissues, and automatically further refine the capability of the AI system algorithm.

The methods and apparatuses described herein may include a pre-procedure analysis that includes training the neural network on CT scans and MRI's, rather than use the arthroscopic 2D image as input to the CNN. The network is trained in a similar fashion to detect landmarks and pathological tissue in these scans. A separate database of CT scans and MRI's may be used where again each scan will have the ground truth bounding box drawn for that landmark. This database may be fed into the CNN so that it may be trained and tested in the same fashion as explained above until an acceptable detection accuracy is met.

In any of the methods and apparatuses described herein, the AI and visual imaging may be used together. For example, any of these apparatuses and methods may employee both classical vision techniques alongside AI based algorithms to determine a 3D location of the robotic arm as well as detect landmarks and pathological tissues from CT and MRI scans while creating a patient specific 3D model of the joint. Two separate neural networks may be trained, e.g., a first having an input dataset general pre-procedure CT scan and MM data from various patients and a second having an input dataset of arthroscopic camera images from various surgeries. The trained neural network in both cases may produce a bounding box of the pixel location of a landmark in the image/scan. In the case of an arthroscopic image, a camera projection technique may be used to reconstruct the depth from the 2D image, providing a 3D location in space, while in the case of a CT and MRI scan, a classification and location of pathological tissues may be produced on the 3D model. A database of images and MRI/CT scans may be built, and as more procedures are performed, this database will continue to grow thereby further improving the accuracy of both AI networks and creating a more robust system. The neural network model may be continuously be refined until minimal error and convergence.

When training each AI network, transfer learning can be used to reduce the time in training. Transfer learning allows the use of knowledge learned from previously trained networks as the basis for our network training. As an example, the Faster Region based CNN with Inception Resnet v2 model neural network can be used, which may be pre-trained on the common objects in context ("COCO") dataset of common objects. Although the image content of the COCO dataset is vastly different from surgical videos and CT/MRI scans, the features learned from the COCO pre-trained network may share some similarity with the medical imaging. By using this knowledge, the neural networks may train faster and have an improved performance, allowing for a higher prediction accuracy.

There are key metrics that can be fine-tuned to allow for improved accuracy while training the neural network as shown in table 1, below.

| Hyper-Parameter | Value |
| --- | --- |
| Learning Rate | 0.0002 |
| Regularization | L2 |
| Optimizer | Momentum Optimizer |

The first key hyper-parameter may be the learning rate, which controls how much adjustment of weights in the neural network is required with respect to the loss gradient. The goal when training a network is to find the minimal error possible, and the learning rate helps define the speed at which this minimum error is found and accuracy of the error. By applying a lower learning rate, the guarantee of finding the lowest error increases, however, training time also increases, so adjusting the learning rate to balance these two factors may be crucial. The next important hyper-parameter is regularization, which is a general class of techniques used to reduce error on the test set by generalizing the model beyond the training set. Many times when training, acceptable loss values are seen in the training phase, but not during the test phase, this is where regularization helps by generalizing the model across training and testing. L2 is one such technique where larger weights in a network are penalized so as to constrain them from dominating the outcome of network. The last important hyper-parameter is the choice in optimizer used to help improve training speed and result accuracy. The momentum optimizer is one such algorithm that helps accelerate finding the minimum training loss by building up velocity when finding this minimum loss. Since a pre-trained model is being utilized, the hyper-parameters set in this model can be used as a starting point, which will give a better result instead of selecting values at random. The parameters can be further tuned as iterations of training continue.

Another factor which allows for improved prediction accuracy it to determine a feature-rich landmark to detect in the surgical video. Two difficulties arise when trying to achieve a high prediction accuracy when looking at surgical videos; first, landmarks may look similar to each other (for example, the glenoid and humeral bone may, to a neural network, look similar in color).

Second, landmarks may not have a lot of features. To overcome these two factors, a landmark may be chosen that has variance in color and shape. For example, the subscapularis tendon in the shoulder may be a good candidate for detection as it has a difference in colors, and distinct color patterns. But this may not be enough, so rather than just labeling images to show the ground truth of the subscapularis tendon, more than one landmark within the same ground truth bounding box may be labeled. For example, instead of only labeling the subscapularis in the training images, it may be better to label both a portion of the subscapularis and a portion of the humeral head where the subscapularis connects. This may provide the neural network with more features to learn from since we have more color features and more shape features to differentiate between other classes.

Thus, in some variations, the methods and apparatuses described herein may determine one or more features to train on based on variations for the one or more features in a factor for the feature within a training set such variance as color, variance in shape, etc. (which may be manually determined or automatically determined). In some variations a second feature may be combined with the first features in which the second feature has a low degrees of variance in the same (or different) factor(s).

FIG. 6 illustrates one method of training an AI for an apparatus (e.g., system), including providing the database of camera images (based on the same camera type as will be used by the robotic apparatus) for which landmarks have been labeled 601. For example, in FIG. 6, the database of camera images with labeled landmarks 601 may be provided, and used to train or test a neural network 603. If the accuracy of the trained network is below a threshold (or acceptable accuracy) 605, then it is retrained/tested; otherwise the network may be used to determine the location of a target and surround it with a 2D bounding box on the image that includes the target 607.

FIG. 7 illustrates a method of training an apparatus including a camera system (e.g., an arthroscopic camera system) for extracting features from two or more pictures (e.g., 2D images), preferably that are separated by a known distance, to determine, based on a common feature within the images, the coordinates (and particularly the depth) of the imaging source, such as a camera, e.g., a camera on the robotic arm, and therefore the coordinates of the robotic arm and/or a device held by the robotic arm. For example, a pair of images 701,703 may be taken from two distances apart (e.g., a known distance between them), as illustrated and described above. The same AI system 705 may then be provided with both of the images (e.g., all of the images), Using these two images, separated by a known distance, one or more landmarks may be detected in these images 707, 707' and a bounding box provided around a target feature(s). The same or a different target feature (or a point or region of the feature) may be extracted 711 for each image. The features between the two images may be matched and depth information may be extracted 713, using the known separation of the cameras between the images, as shown in FIG. 4, and described above. Thus, the position of the robotic arm in space may be determined 715.

When using an image based CNN to determine the location of a bone landmark, there may be a lack of orientation understanding of that landmark. For example, a humeral head landmark can be detected by the CNN architecture described above regardless of whether the camera is looking at the humeral head from the front, side, top, or even upside down. The information received in all cases may be an x, y, z position in space, but there may be no orientation understanding. A second neural network could be employed to predict the shape of different portions of the bone landmark by predicting, e.g., the curvature of the landmark from the 2D image. Because a bone or other landmark within the shoulder can look similar in features such as color or texture, it may be advantageous to use curvature to help the detection process.

Figure 13:
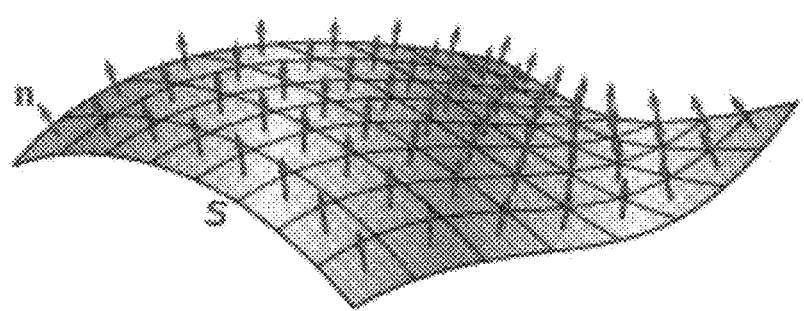
FIG. 13 shows one example of a surface normal (e.g., a distribution of surface normal vectors for the surface shown.

A neural network may output surface normals at different points across the surface of the landmark (e.g., 1, 2, 3). A surface normal is a vector that projects perpendicularly from a point on the surface (see FIG. 13). The network may be trained to predict the surface normals for smaller portions of the detected landmark. Since the shape of different areas of a landmark may be vastly variable, this information could be used to determine which part of the landmark is being viewed. For example, if a humeral head was detected in the first network, this second neural network would predict which portion of the humeral head is being viewed by the camera (i.e. top, front, side, etc.) based on the predicted surface normals. Since each landmark detected may predict its shape and viewing point, an understanding of general landmark location within the shoulder can be generated.

For example, if the first network detects a humeral head, and the second network predicted the front of the humeral head, then it would be expected that the scapula should be detected to the right of the humeral head. This system of neural networks would aid in verifying the general locations of different bone landmarks, further increasing the overall confidence of the camera's location within the shoulder.

The methods and systems described herein therefore allow the architecture of a CNN to find the surface normals, and then use this information to determine what kind of bone landmark is being imaged, and exactly where these bone landmarks lie in relation to one another. By determining the kind of bone the system is looking at, this information can be cross-referenced with information received by the first AI network (e.g., on bone type) to determine if the system is detecting the correct landmark. This can also be used to build an understanding of what we are looking at from an orientation stand point. Thus, essentially a first neural network may be used to identify the landmark (e.g., as bone) while the second neural network may be used to determine the orientation of the landmark. If the network determines the curvature of a humeral head from different angles based on our training, this can be matched to the current view of the humeral head.

This could provide more information to determine if the system is looking at it (the landmark) from the top, bottom, and/or side. If this information is determined for or from the landmarks near the humeral head, it may help better understand where the system (e.g., robotic arm) is in the shoulder. Relying exclusively on an image based AI network to determine the position, although it may detect a humeral head as a humeral head whether it was looked at from the top, side, front, or even upside down may not give us an exact position in space; the use of the second AI network to determine orientation may build a map of where bone landmarks lie in relation to one another to better understand the orientation and reference frame.

Although the angle at which the camera is positioned relative to some local frame of reference may be known, the angle the camera is viewing the landmark from may not be known. By knowing the surface normals of the landmark, the system can match the surface normal of the camera with the parallel surface normal from the landmark, thereby identifying at which angle the camera is viewing the landmark. This may give both the position and orientation of the camera with respect to the cone landmark.

The techniques described herein may also additionally optimize/reduce error by ensuring the orientation with respect to the expected landmark from an x, y, z network. The use of these techniques may also ensure the correct landmarks from an x, y, z network; the model may assume it is one of several landmarks with a probability of each option and this technique may improve filtering. In some variations, these methods may also ensure that the landmark from an x, y, z network is not an artifact (e.g., there may be fluids/tissue/bubbles all over the joint and the expected curvature will help clarify it is in fact a landmark). Finally, these techniques may optimize the orientation of the instrument being used; for example, by knowing the curvature the system amy further optimize insertion of, e.g., a suture anchor beyond the precision you would get with just network x,y,z.

Figure 14:
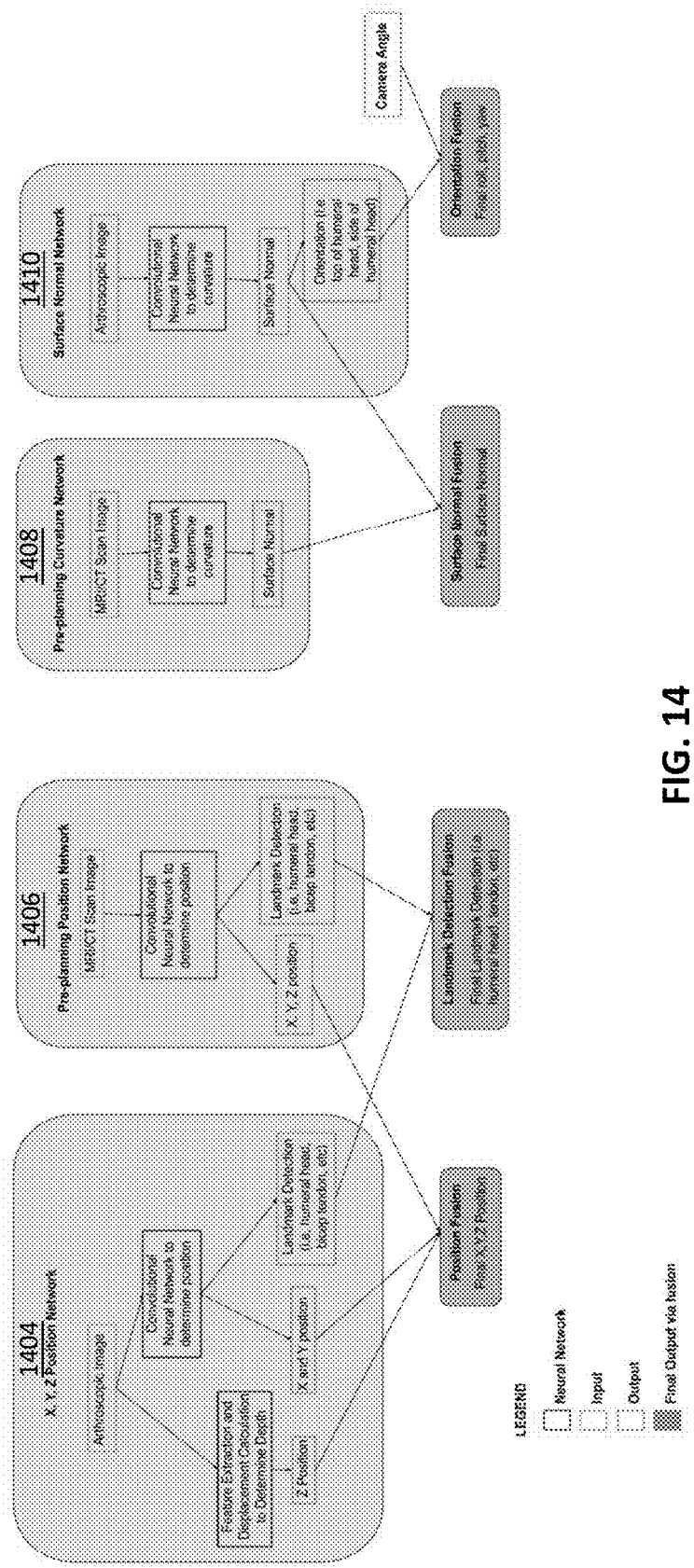
FIG. 14 schematically illustrates one example of a method (or a system including the method) for operating a robotic surgical device. This method or a system for performing it may be used to guide, steer and/or navigate a robotic tool (e.g., a robotic arm or tool held by a robotic arm).

FIG. 14 illustrates one example of a system and method that may include all or some of these techniques. For example, in FIG. 14, a system may include multiple machine learning networks for identifying different aspects of the images in order to identify landmarks and the orientation of landmarks, and ultimately determine the relative position of the landmarks to, e.g., a robotic arm or other component. In some variations the system includes an X, Y, Z position network 1404 that receives arthroscopic images and may extract features from the arthroscopic images, as well as calculate displacement (e.g., from different locations) to determine an estimate of depth (z-position) of an object (e.g., landmark, such as bone) in the images. A convolutional neural network (CNN), that is trained as described above, may be used to identify one or more landmarks, including the X, Y position of these landmarks (such as bone, e.g., humoral head, bicep tendon, etc.).

Alternatively or additionally, another network 1406, e.g., a pre-planning position network, may be used with the X, Y, Z position network, and may use MRI/CT scanned images of the patient with a trained CNN to determine the position (e.g., X, Y, Z position), and/or landmark detection, of landmarks such as bone landmarks (e.g., humeral head), bicep tendon, etc. In some variations the pre-planning position network may be used with the X, Y, Z position network; in these cases the positional information from both may be combined, e.g., to form position fusion (final X, Y, Z position) information and/or Landmark detection fusion (final Landmark Detection). The pre-planning position network may be used prior to performing an operation using a robotic arm, for example, while the X, Y, Z position network may be used with images taken (e.g., arthroscopic images) during the procedure.

The X, Y, Z position network and/or the pre-planning position network may be used with one or more additional networks trained to determine orientation and/or surface normal information, as described above. For example, either or both a pre-planning curvature network 1408 and/or a surface normal network 1410 may be used, e.g., to provide surface normal information.

For example, a pre-planning curvature network may use as input images, such as patient-specific MRI/CT scan images an may use the trained CNN to identify surface normal information for the tissue, including for landmarks. The CNN may be trained as described above.

The surface normal network 1410 may use arthroscopic images (including the same arthroscopic images used for the X, Y, Z position network) with a trained CNN to determine curvature of the structures in the images (including landmarks). This surface normal information may bused with the position information (e.g., X, Y, Z position), including in some variations position fusion information. In some variations the surface normal information from both the pre-planning curvature network and the surface-normal network may be combined to form surface normal fusion data ("final surface normal" information).

In some variations, the surface normal network may determine orientation as discussed above. For example, the surface normal network may use the identified surface normal information to determine orientation (e.g., of the landmark or other structures from the arthroscopic images); the orientation information may be combined with the camera angle information from the related arthroscopic images to determine orientation fusion data (e.g., final roll, pitch, yaw information) of the landmarks or other structures. Either or both the surface normal information and/or the orientation information (e.g., pitch roll, yaw) may be used along with the position information and/or the landmark detection information to plan and/or steer the motion of the robot during a procedure.

Example 1

Figure 8:
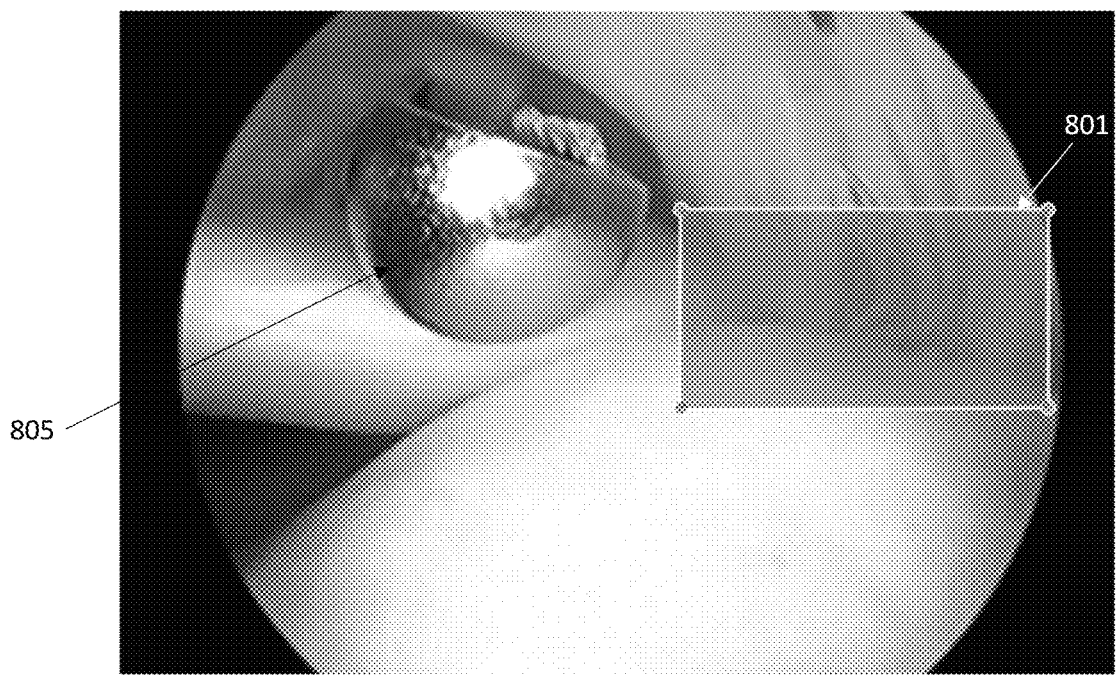
FIG. 8 is an example of identification of a target region in a series of 2D images as described herein; in this example, the images are arthroscopic images of a patient's shoulder and the identified target region(s) is the subscapularis and the humeral head.

FIG. 8 illustrates one example of the methods described above, in which an image is taken by a camera (an arthroscopic view of a shoulder). The system may accurately detect the attached portion of the subscapularis to the humeral head, as shown in the bounding box 801 marked in FIG. 8. This identified region from each of the images may then be used to determine the location of the tool 803 and/or robotic arm. As the robotic arm and/or tool move, the images may be constantly updated. In some variations, multiple images may be taken and identified from different positions to triangulate the depth and thus the x, y, z position of the tool and/or robotic arm. In this example, the system recognizes both the subscapularis and the humeral head.

In general, any appropriate end effector devices ("end effector") may be used. For example, an end effector device may be a custom end effector device. The dimensions of the end effectors may be known (e.g., preprogrammed, predetermined, etc.) by the system so that arm positioning takes into account the physical size of the end effector in locating positions relative to the physiologic target. The end effectors may ideally attach and detach easily, securely, and precisely to the robotic arm(s). The end effectors may have contact with live tissue and may therefore be sterile and/or sterilizeable. The end effector could be made so that it could be re-used between procedures, e.g., by sterilizing using hospital sterilization equipment, or it could be provided sterile for single use. End effectors may include devices for holding instruments, such as cannulas, touch positioning instruments, cameras, etc. End effectors or the associated robotic arm could also incorporate sensors other than or in addition to optical sensors. For instance, an end effector could have a motor and collet that attaches to a drill or burr for bone removal replacing current handheld drills. This may advantages not only for stability and positional precision, but may also provide rotational speed feedback, torsional force feedback and/or force feedback. This feedback could include preset limits that would protect from bone damage that could affect the ability of an implant to securely attach or could prevent excess bone removal or other damage. Additional sensors such as thermal sensors could ensure that bone is not thermally damaged. This could include a thermistor, thermocouple, infrared thermal system or other system to monitor temperature. The temperature sensor may be configured to detect the temperature of the end effector (e.g., drill, burr, saw, etc.) and/or the interface between the body region and the end effector. This could also include burrs or drills that incorporate these sensors or otherwise couple the temperature at the tip of the probe back to a sensor in the end effector or robotic arm. For instance a copper or aluminum core could be integrated into the burr or drill that is in contact with the material of the burr or drill tip, but is thermally insulated along the burr or drill shaft length, and may be exposed to an infrared measurement system in the end effector would enable monitoring of the temperature of the tip of the burr during the procedure. This may be coupled so the speed and force of the burr/drill may automatically slow or stop if the temperature approached temperature that could thermally damage bone or other tissue.

In an of these end effector device, which may be held by, mounted to or otherwise coupled with the robotic manipulator (e.g., arm), may include a quick change collet for connecting to the robotic manipulator. The end effector may therefore be removable and re-sterilizable (e.g., autoclaved). The end effector may be controlled by the robotic system, and the user/operator may have the ability to override; in some variations the robot may be constrained from overriding the user (e.g., physician). In some variations, one or more safety overrides may be included, including a safety override for temperature as described above. Any of these apparatuses may include a torque override for overriding based on torque (e.g., torque, as detected by a sensor on the end effector and/or robotic manipulator) exceeds a predetermined threshold. Similarly, safety overrides may be based on force detection and/or positon detection. Sensors (e.g., force sensors, position sensors, etc.) on the robot and/or end effector may be used as inputs to the apparatus (e.g., system) that my determine/detect override information.

The end effector(s) may include a power supply and/or they may be powered through or by the robotic arm. In some variations, the power supply may be a rechargeable power supply. In some variations the end effector may be powered through a power connection on the robotic arm or the coupling to the robotic arm. The power supply to the end effector may be separate from the robotic arm control/power supply.

Figure 10A:
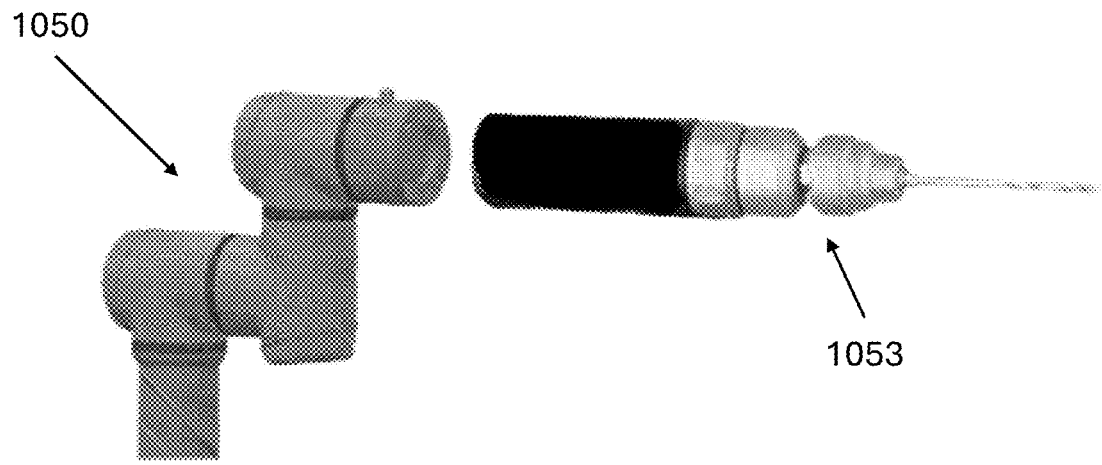
FIG. 10A illustrates one example of an end effector coupling to a robotic manipulator (e.g., arm)

For example, FIG. 10A illustrates one example of an end effector configured as a drill 1053 that is shown coupling/connecting to the distal end of a robotic manipulator 1050 (e.g., shown in as a robotic arm in this example). The drill may include a wired/coupled and/or wireless connection to the robotic apparatus, including the control system that may also control operation of the end effector, such as the drill shown in FIG. 10A.

In variations of the end effectors including a moving component, such as a drill, saw, burr, etc., a speed control may be provided. In some variations the speed control may be a variable speed control. For example, the speed control may be pre-set and/or adjustable. In some variations, the speed control may be triggered by position (e.g., position of the arm relative to the target, which may be detected by the system as described herein).

In general, the apparatuses described herein may include one or more feedback means, such as visual feedback in the augmented reality (e.g., color, flashing, etc.), and/or tactile feedback (vibration, nudging, etc.), audio feedback, etc.

As described above, any of the end effectors described herein may include a temperature sensor. In some variations the temperature sensor may be configured for non-contact detection of temperature from the tissue, the device/end effector and/or the interface between the end effector and the tissue. For example, in some variations a non-contact sensor such as a temperature sensor may be included near the tip of the end effector; for example, when the end effector is a drill the temperature sensor may be included near the drill tip (e.g., FLIR on arm). In some variations the temperature sensor may be positioned away from the tip (e.g., temperature may be conducted back to or behind the connecting collect with an insulated conductor, e.g., from the tip or a more distal region). Any appropriate sensor may be used, including IR, thermocouple, thermistor, etc. For example, a thermistor may be near the collet. The temperature data may be used to control the robotic apparatus and/or the end effector. For example, the temperature information may be used to generate max/min values, PID feedback, etc.

Any of the apparatuses described herein may include position information for the one or more end effectors. For example, position information may be visually determined, e.g., by camera data, from a camera either on the end effector and/or on the robotic manipulator. The position may be determined by the controller (e.g., knowing the arm position and end effector/tip geometry may allow the robotic apparatus to determine the position of the tip/location of the tip.

Figure 9A:
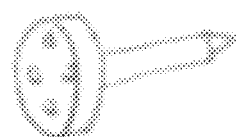
FIGS. 9A-9E show examples of end effectors that may be used.
Figure 9B:
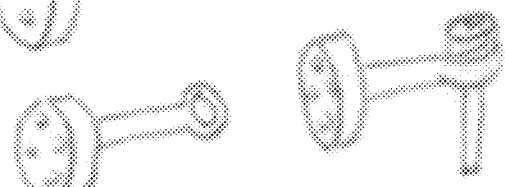
Figure 9C:
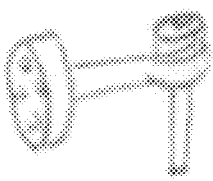
Figure 9D:
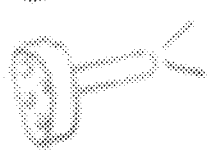
Figure 9E:
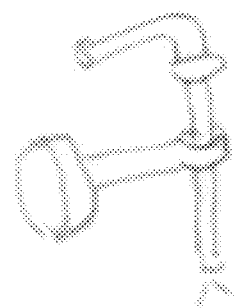

Any of the end effector devices described herein may be touch end effectors. For example, a touch end effector may include a probe that may contact the tissue. FIGS. 9A-9E illustrate examples of end effectors. For example, FIG. 9A is a touch end effector including a probe end. FIG. 9B is a cannula/instrument grasping end effector (FIG. 9C shows the end effector of FIG. 9B grasping a cannula. FIG. 9D is an example of a camera end effector. FIG. 9E is an example of an end effector with an integrated instrument (e.g., a camera).

Figure 10B:
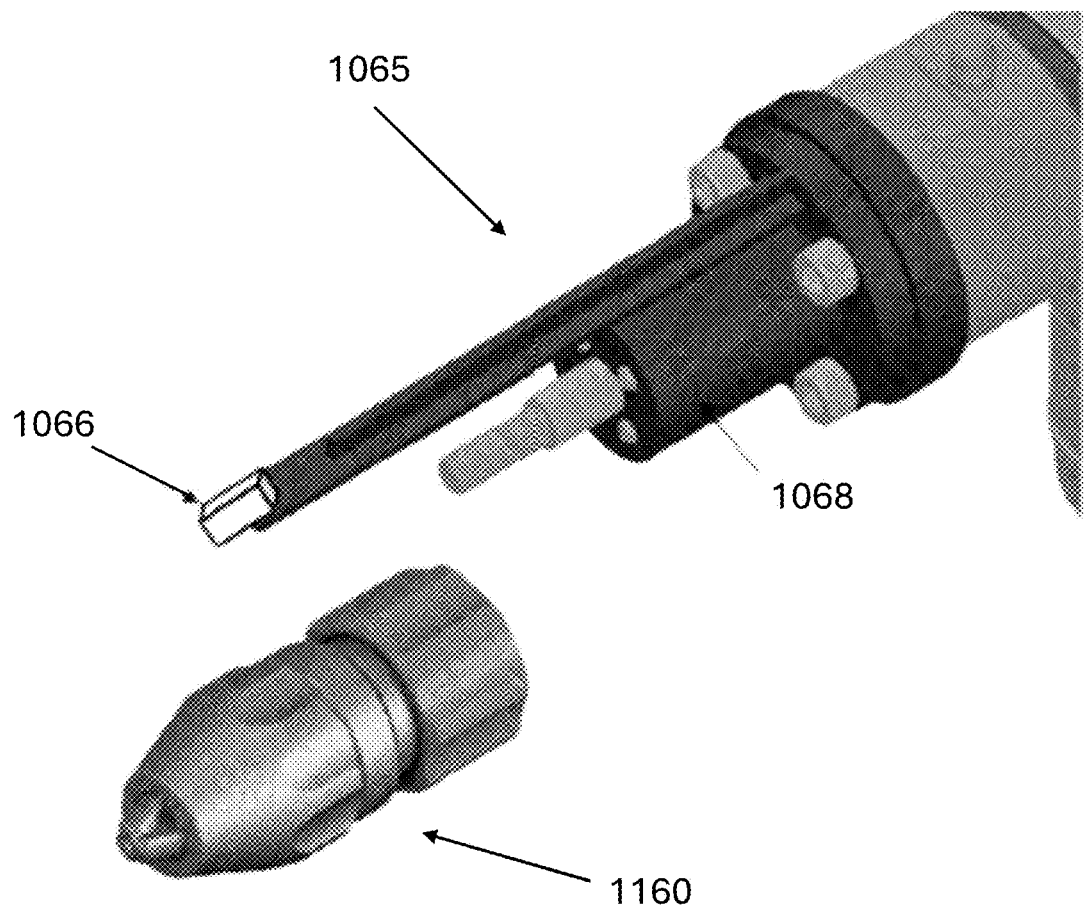
FIG. 10B is an example of an end effector coupled to a robotic manipulator (e.g., arm).
Figure 10C:
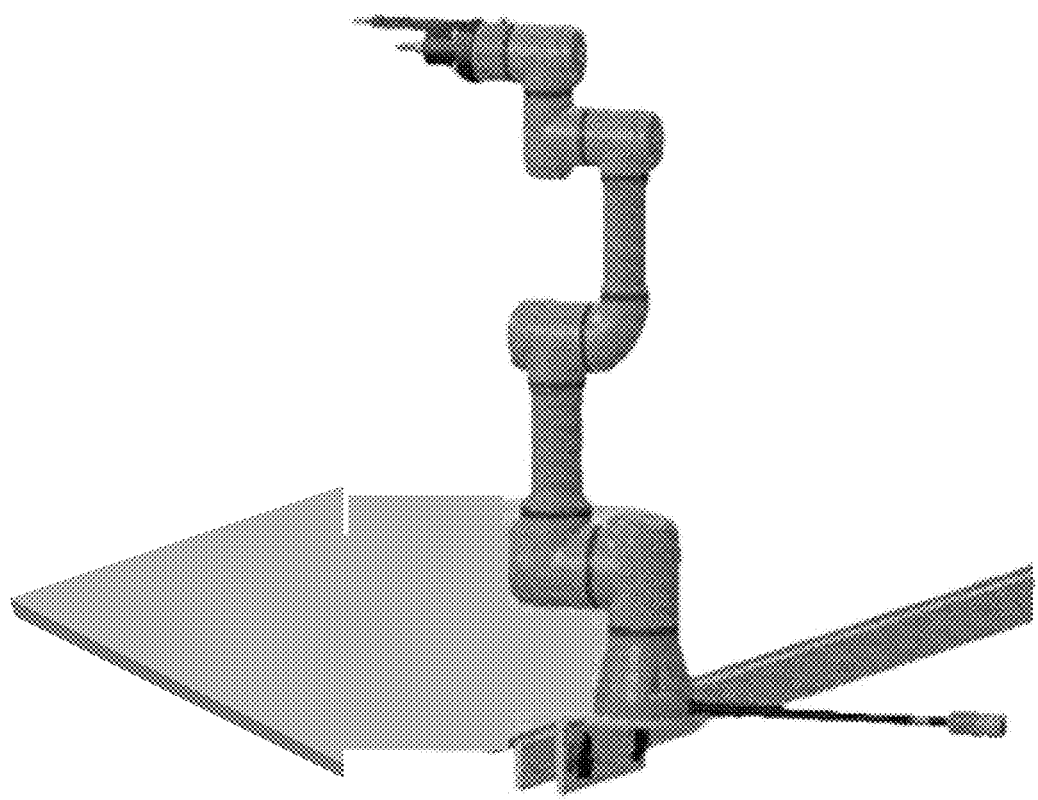
FIGS. 10C and 10D show a robotic arm such as the one shown in FIG. 10B mounted to a bedside (e.g., operating table) in side and top perspective views, respectively.
Figure 10D:
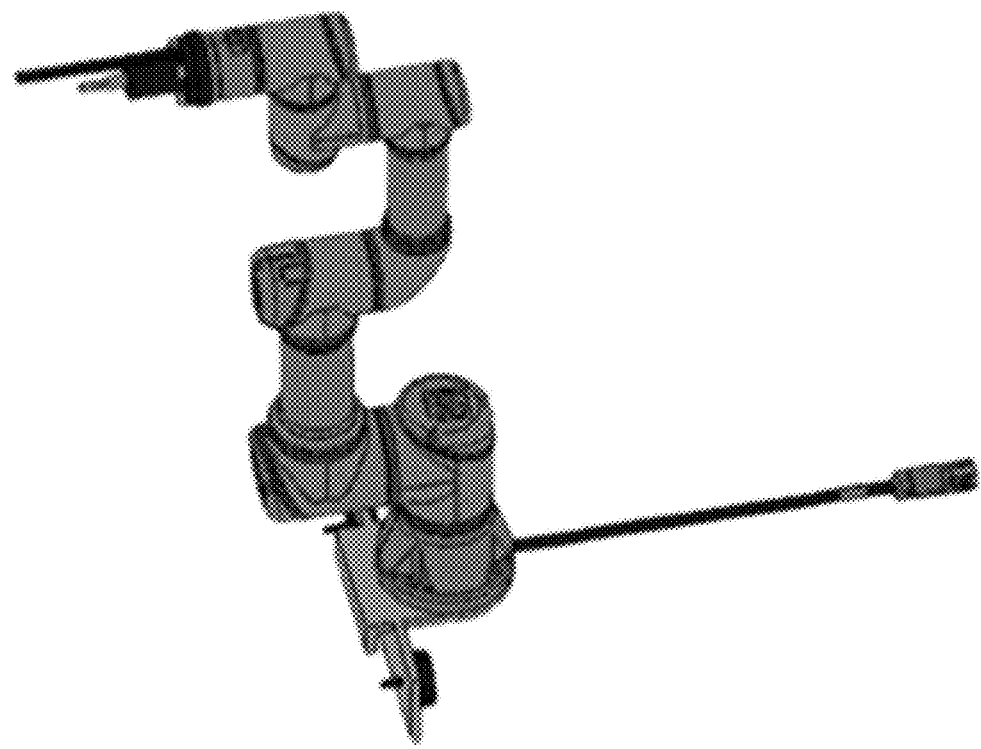

FIGS. 10B-10D illustrate one example of an end effector shown as a drill 1060. In this example the end effector frame 1065 couples (e.g., bolts) to an end of the robotic manipulator and includes a driver (e.g., DC motor 1068) to drive rotation of a drill that mounts, e.g., via collect mount 1060 on a spindle, as shown. The end effector mount may also include a sensor 1066 (e.g., camera) that couples to the tip of the end effector (e.g., shown bolted in FIG. 10B). Different sensors may be used, including swapping them out. For example, IR cameras (heat detection) may be used with multiple different lines of sight.

FIGS. 10C and 10D illustrate a robotic apparatus, including a robotic manipulator (arm) 1070 such as the one partially shown in FIG. 10B, that is mounted to a patient's bedside. FIG. 10C is a side perspective view and FIG. 10D is a perspective view.

AR Feedback to Physician

In general, it may be advantageous to include augmented reality (AR) feedback for the physician in any of the methods and apparatuses described herein. For example, AR may allow a physician to assess where they are (e.g., in the patient) without having to manipulate the imaging camera. Thus, a system may be constructed with AI data, from pre-recorded MRI/CT data, or from other database sources. The AR image(s) could be displayed on a headset or on a monitor, such as the monitor that is displaying the current camera view. Tissue image layers may be presented in such a way to facilitate the procedure; this could be image layers that could be turned on or off, layers that could change in transparency, or other useful characteristics. Tissues such as epidermis, sub-cutaneous fat, sheaths, muscles, cartilages, tendons, bones, lymphatic systems, vascular structures and nerves could be displayed in different color or patterns. This may assist the surgeon in accessing and assessing the surgical procedure with ease. This may allow a fast learning curve, allowing even less-experienced doctors to be better equipped to operate independently with the help of these tools. This may also be used for simulation of surgeries and/or for training of medical residents for surgeries, and/or for continuing medical education for newer procedures.

Figure 11A:
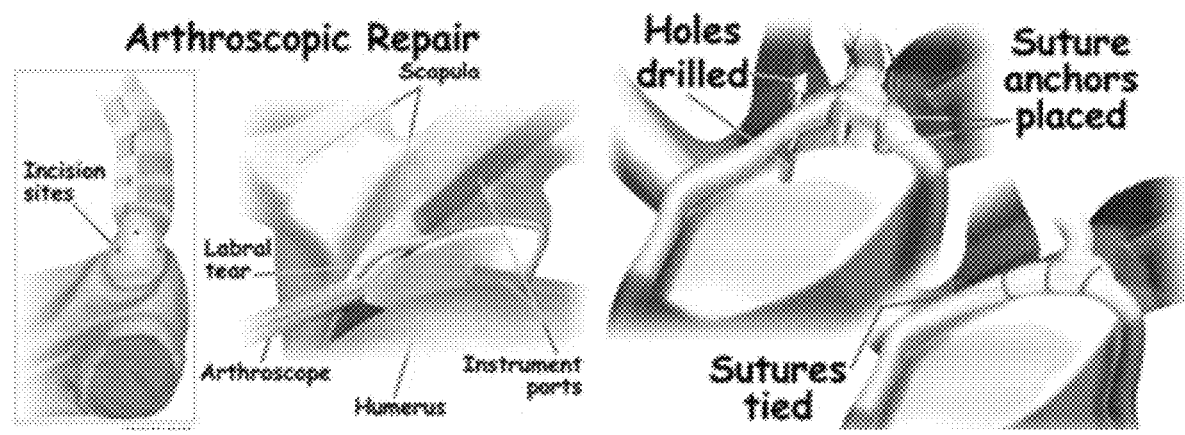
FIG. 11A is an example of procedure locations, interventions, etc. that may be planned as described herein.

Any of the methods and apparatuses described herein may also or alternatively have associated procedure planning tools. These tools could be constructed from pre-procedure MRI or CT data. These could be used to precisely plan procedure even the location of screws or other procedural elements that used in reconstruction. The motions and loading of the joints at the end of the procedure could then be mapped out in advance. The procedure could then be executed more efficiently, and the result may be precise and durable. FIG. 11A illustrates examples of procedure locations, interventions, etc. that may be planned as described herein.

Figure 11B:
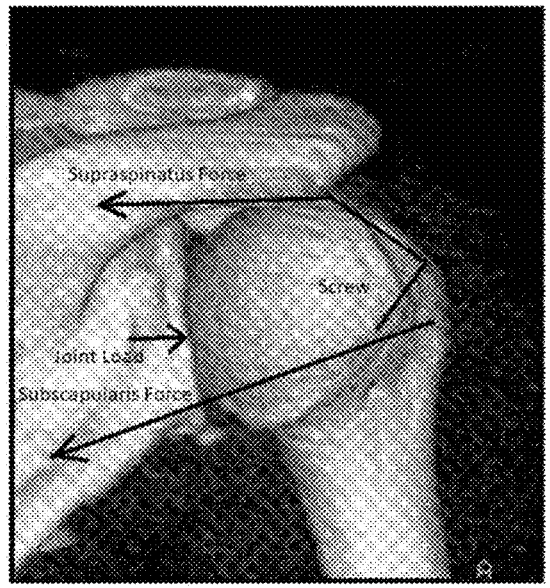
FIG. 11B is an example of 3D models of the system and/or patient tissue that may be generated as described herein.

Any of these methods may also include one or more 3D models. That may be constructed from images. These 3D models may be constructed from images. Simulations of motions, loads and interventions may be provided and performed using the 3D models. For example, FIG. 11B illustrates examples of 3D models, and in particular examples of how 3D models can be constructed from images. Simulations of motions, loads, and interventions can be performed.

For example, pre-procedure MRI or CT data slices may be used to determine a 3D model of the patient's tissue that can be constructed from the slices. In the case of an orthopedic joint replacement procedure, pre-procedure MRI or CT data may be used to prepare a 3D model of the joint, which could also show pathological tissues like calcifications, osteophytes, pannus, bone erosions. Also, this 3D model may allow preplanning of the surgical procedure and different joint implants may be placed/overlapped onto the 3D model to check for the best fit for the patient. The range of motion and joint loads can also be simulated with the help of this 3D model. The plan may then be saved for intra-operative review.

Figure 12:
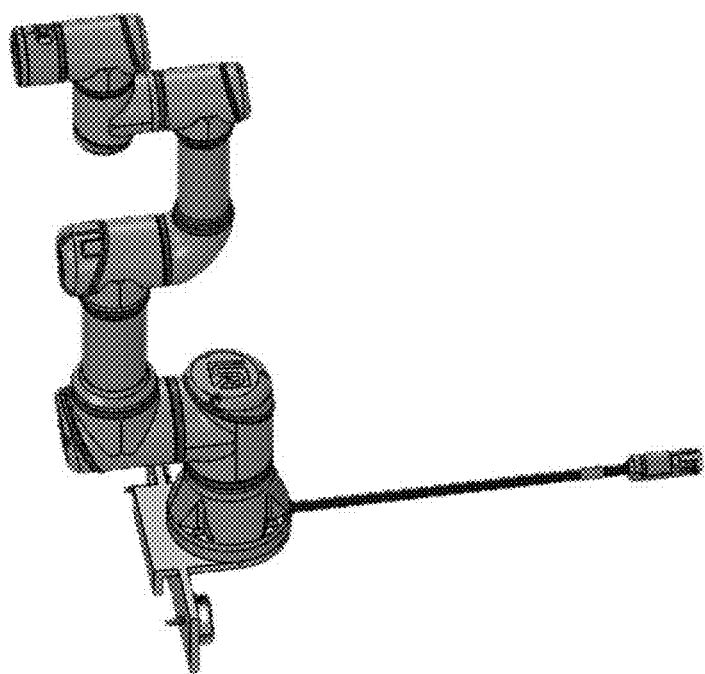
FIG. 12 is an example of a robotic arm including a clamp.

Any of the Master Robotic Arms described herein could have Six Degrees of Freedom (6DOF); hence it may help ease the surgical procedures and make them more swift and agile. A Six Degrees of Freedom robotic arm may provide dexterity and may help access hard to reach places in the procedures, for example, during shoulder replacement surgery, the Scapula Bone comes in between and the areas not to be even slightly disturbed are the highly sensitive brachial plexus and vascular structures, that are located onto the medial side of the coracoid process. Without 6DOF, it would be hard to reach certain areas of the joints. FIG. 12 illustrates one example of a 6DOF robotic arm.

Any of the apparatuses and methods described herein may be inter-operative. A robotic system could help in assessing the accuracy of the procedure and its deviations from the planned procedure. In case of any deviations, a robotic system could assist the surgeon, by providing real-time view of the operation plane on the 3D model. For example, in the case of knee replacement surgeries, the surgeon can also perform valgus and varus stress tests during the surgery and check the stressed range of motion under these stress test scenarios on the 3D model. With the help of these stressed range of motion tests, it may be easier to fix the implant and assess the post-operative range of motion. The live feedback may allow a surgeon to modify the surgery in real-time by making adjustments. Similarly, in case of shoulder replacement surgeries, the robotic system may help in providing real-time view of glenoid retroversion and inclination, and the system can also show in real-time the reaming and drilling depth and screw placement positions. This real-time feedback may give the surgeon added ability to adjust surgical plan intraoperatively, offering more surgeon flexibility during these complex procedures. The robotic system may help reproduce the preoperative plan with precise execution intraoperatively and helps the surgeon by providing live feedback, allowing for real-time adjustments.

In shoulder replacement surgery, one of the common challenges faced by the surgeon is to assess the center line for the glenoid placement, this could easily be solved by the use of robotic system and the central peg hole could be made with the help of live-guidance of the robotic navigation system. A robotic system as described herein could also help provide clear visibility into the glenoid vault in real-time and thus provide a more consistent, accurate glenoid placement in both standard and in challenging cases of compromised rotator cuffs. Any of the robotic systems described herein could help in a more accurate glenoid placement and thus minimize complications and increase implant survivability for the patients. With the help of any of these robotic apparatuses (e.g. systems), the shoulder replacement surgery may be performed according to the planned implant placement, thus giving accuracy in the version, inclination, tilt and implant placement, this shall be a great improvement over standard surgeries or even surgeries performed with patient-specific instrumentation.

A robotic system arm as described herein may have narrow end edges with high degree of precision, thus there may be minimal resection and minimal release of the ligaments. For example, in shoulder replacement surgery, there may be minimal release of the subscapularis tendons and ligaments, and the insertion points of the rotator cuffs may be maintained.

A robotic surgical navigation system as described herein may index itself in relation to the bony landmarks. Thus, when the patient's joint is moved, the robotic surgical system can reposition itself to point towards the surgical site. For example, in the case of shoulder replacement surgery, the humerus may be dislocated anteriorly several times during the procedure to prepare the head of the humerus for the implant and proper positioning in the glenohumeral joint. With the help of planning tools and intra-operative visualization, a surgeon can virtually position the implant and balance the soft tissue in relation to the implant even in cases of joint movements during surgery. Similarly, in case of knee replacement surgery, in order to do the valgus and varus tests, the knee joint is moved, and thus the stressed range of motion tests may be carried out. In these cases of movement of the patients' joint, the robotic surgical navigation system may help re-index itself in relation to the joint of the patient and reorient itself back in relation to the surgical plan.

Robotic systems as described herein may help in reducing damage to healthy tissues and minimize scar and adhesion formations due to increased precision during surgery. This may lead to minimal pain and suffering for the patient, faster recovery, custom fit, extra flexion and range of motion for the patient and shorter hospital stays. The rehabilitation of such patients could be easier and there could be lesser chances of revision surgeries.

Another use of robotic apparatuses described herein in joint replacement surgeries would be in the case of challenging cases, post-fracture cases or cases of revision surgeries. For example, in case of a revision shoulder replacement, often the position of the axillary nerve is misplaced and it is difficult to identify the axillary nerve in the presence of scar tissue and adhesions. It is important to avoid damage to the axillary nerve during the incisions. Similarly, in cases of shoulder replacement surgeries in patients with prior shoulder fractures, the bone structure, axillary nerve and the rotator cuff is often misaligned in comparison to a healthy shoulder joint. The incisions to the fascia should be such that the axillary nerve is salvaged and away from the path of the operation. In such cases, any of the robotic systems (including AI) described herein, may result in added accuracy in identifying the bony landmarks, tissue landmarks such as the nerves, tendon insertions onto the bone even in the presence of scar tissue and adhesions.

The robotic systems and methods described herein may also or alternatively completely remove the process of cutting the bone surface with bone saws, instead the robotic arm may have a burr at the end of the arm and it may burr away the arthritic tissue and thus prepare the bone surface for the implant. For example, in the case of shoulder replacement surgery, the head of the humerus may be cut using a sagittal bone saw, this often leads to healthy bone loss. The robotic systems described herein may help in preparing the head of the humerus by just burring away the arthritic tissue and osteophytes. The burr may also help drill precise hole in the humerus to help in placement of the implant. Similarly, the glenoid surface may be prepared by the robotic burring system and then the central peg hole may be burred accurately at a point on the center of the glenoid such that after calculating the strength of the rotator cuff system of the joint and aligning the center line for the glenoid placement at the desired orientation.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of operating a robotic surgical device, the method comprising:
   determining a position of one or more landmarks from an image of a first field of view of a camera associated with the robotic surgical device using a first neural network, further wherein the first neural network determines the depth of the one or more landmarks using an image of a second field of view that overlaps with the first field of view; and
   determining a surface normal for the one or more landmarks using a second neural network; steering the robotic surgical device using the position and surface normal for the one or more landmarks; and
   determining the position of a robotic arm of the robotic surgical device or of a device held in the robotic arm by triangulating between the image of the first field of view and the image of the second field of view.

2. The method of claim 1, wherein the first and second neural networks operate in parallel.

3. The method of claim 1, further comprising determining the orientation of the one or more landmarks relative to the robotic arm using the surface normal and a camera angle of the camera.

4. The method of claim 1, wherein determining the position of the one or more landmarks comprises using a third neural network operating on one or more external scan images to detect a pre-planning position of the one or more landmarks and wherein the position of one or more landmarks comprises a combination of a position information from the first neural network and the pre-planning position from the third neural network; and
   detecting the one or more landmarks from the image of the first field of view of the camera using a combination of a putative landmark detection from the first neural network and landmark detecting from the third neural network.

5. The method of claim 1, further comprising detecting the one or more landmarks from the image of the first field of view of the camera using the first neural network.

6. The method of claim 1, wherein determining the surface normal for the one or more landmarks using the second neural network comprises using the image of the first field of view, the second field of view or both the first and second field of view.

7. The method of claim 1, wherein determining a surface normal for the one or more landmarks using the second neural network comprises combining surface normal information from the second neural network with surface normal information from a fourth neural network.

8. The method of claim 1, further comprising, detecting pathological tissues from the first field of view and displaying an image of the image of the first field of view in which the pathological tissues are marked, wherein detecting pathological tissues comprises determining from a plurality of CT and MRI scans a classification and location of pathological tissues on a 3D model.

9. The method of claim 1, wherein detecting one or more landmarks comprises receiving CT and MRI scans to create a patient specific 3D model of a joint.

10. The method of claim 1, further comprising selecting two or more landmarks on which to train the first neural network, the second neural network, or both the first and second neural network, wherein at least one of the landmarks is selected to for having a feature with high variance and a second landmark is selected for having a feature with a low variance.

11. A method of operating a robotic surgical device, the method comprising:
    determining a position of one or more landmarks within an image of a first field of view of a camera associated with the robotic surgical device using a first neural network,
       wherein the first neural network determines the depth of the one or more landmarks using an image of a second field of view that overlaps with the first field of view; and
       determining a surface normal for the one or more landmarks using a second neural network operating in parallel with the first neural network; and
       determining the orientation of the one or more landmarks relative to the robotic arm using the surface normal and a camera angle of the camera; and
       steering the robotic surgical device using the position and surface normal for the one or more landmarks.

12. The method of claim 11 further comprising, detecting one or more landmarks within the image of a first field of view of a camera associated with the robotic surgical device and within the image of a second field of view that overlaps with the first field of view is by an artificial intelligence (AI); and
    determining the position of a robotic arm or a device held in the robotic arm is by triangulating between the image of the first field of view and the image of the second field of view.

13. The method of claim 12, further comprising detecting pathological tissues from the first field of view and displaying an image of the image of the first field of view in which the pathological tissues are marked.

14. The method of claim 13, wherein detecting pathological tissues comprises determining from a plurality of CT and MRI scans a classification and location of pathological tissues on a 3D model.

15. The method of claim 14, further comprising creating two separate neural networks to identify the one or more landmarks within the images of the first and second fields of view.

16. The method of claim 15, further comprising producing a bounding box around a pixel location of the one or more landmarks in each of the in the images of the first and second fields of view.

17. The method of claim 16, wherein determining the position of the robotic arm or the device held in the robotic arm by triangulating between the image of the first field of view and the image of the second field of view comprises reconstructing a depth of the landmark relative to the robotic arm or the device held in the robotic arm.

18. A system comprising:
a robotic arm;
one or more processors; and
memory coupled to the one or more processors, the memory configured to store computer-program instructions, that, when executed by the one or more processors, perform a computer-implemented method comprising:
determining a position of one or more landmarks from an image of a first field of view of a camera associated with the robotic surgical device using a first neural network, further wherein the first neural network determines the depth of the one or more landmarks using an image of a second field of view that overlaps with the first field of view; and
determining a surface normal for the one or more landmarks using a second neural network; and
steering the robotic surgical device using the position and surface normal for the one or more landmarks.

19. The system of claim 18, wherein the computer-implemented method further comprises determining the position of a robotic arm of the robotic surgical device or of a device held in the robotic arm by triangulating between the image of the first field of view and the image of the second field of view.

20. The system of claim 19, wherein the computer-implemented method further comprises determining the orientation of the one or more landmarks relative to the robotic arm using the surface normal and a camera angle of the camera, and
wherein determining the position of the one or more landmarks comprises using a third neural network operating on one or more external scan images to detect a pre-planning position of the one or more landmarks and wherein the position of one or more landmarks comprises a combination of a position information from the first neural network and the pre-planning position from the third neural network.

* * * * *